United States Patent [19]

Torsi

[11] 4,125,558
[45] Nov. 14, 1978

[54] METHOD FOR THE MANUFACTURE OF THE CIS-2-HYDROXY-2-PHENYL-R-1-CYCLOHEXANECARBOXYLIC ACID

[75] Inventor: Cosimo B. Torsi, Pisa, Italy

[73] Assignee: Guidotti Internationale S.A., Italy

[21] Appl. No.: 739,715

[22] Filed: Nov. 8, 1976

[30] Foreign Application Priority Data

Nov. 12, 1975 [IT] Italy ............................... 29221 A/75

[51] Int. Cl.² ............................................. C07C 65/14
[52] U.S. Cl. ................................. 562/418; 260/340.3; 568/807
[58] Field of Search ........................ 260/520 E, 340.3; 568/807

[56] References Cited

PUBLICATIONS

Zimmerman, H. E. et al., J.A.C.S., 76, #9, 2285–2290, 1954.

Primary Examiner—Paul J. Killos

[57] ABSTRACT

A known effective choleretic, cis-2-hydroxy-2-phenyl-r-1-cyclohexane carboxylic acid is obtained with a novel method wherein 1-phenylcyclohexene is reacted with formaldehyde in formic acid or mixture of formic acid with other solvents. The reaction mixture is hydrolyzed (alkaline hydrolysis) to provide a substituted cyclohexanol concurrently with a substituted dioxan. The substituted diol is separated from the substituted dioxan and finally oxidized to obtain the expected acid.

8 Claims, No Drawings

METHOD FOR THE MANUFACTURE OF THE CIS-2-HYDROXY-2-PHENYL-R-1-CYCLOHEXANECARBOXYLIC ACID

This invention relates to a novel stereo-selective method for the preparation of the cis-2-hydroxy-2-phenyl-r-1-cyclohexanecarboxylic acid (which is also known, under the common, nonproprietary Italian and international name of cyclooxylic acid), having the formula:

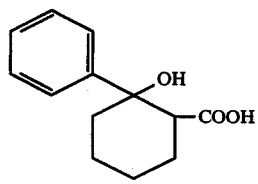

(1)

The configuration and the form of such a compound (demonstrated by IR spectrometry and nuclear magnetic resonance studies) are indicated in the following formula:

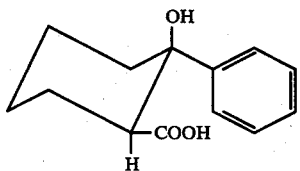

(1a)

Studies which have been carried out in the past have shown that this acid possesses a pronounced choleretic action (see, for example, U.S. Pat. No. 3,700,775).

The preparation of the product (1) which is the subject-matter of the present invention has been described for the first time by H. E. Zimmerman and J. English, Jr. in the J. Amer. Chem. Soc., 76, 2289 (1954) as indicated in the Pattern I.

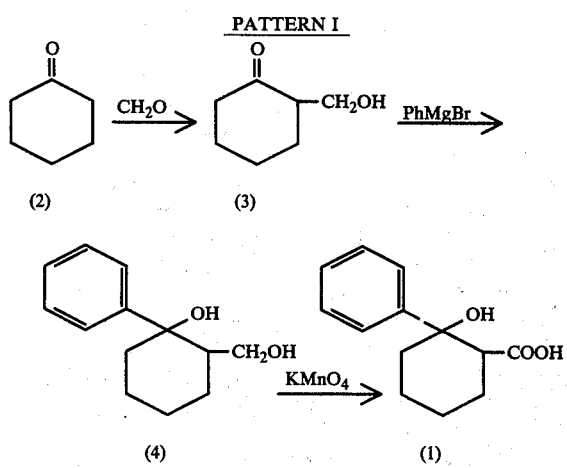

By condensing cyclohexanone (2) with formaldehyde, the 2-hydroxymethylcyclohexanone (3) is obtained, wherefrom, by reaction with phenylmagnesium bromide, 1-phenyl-cis-2-hydroxymethyl-r-1-cyclohexanol (4) is prepared, the latter being subsequently oxidized with potassium permanganate into the acid (1).

A different synthesis of the acid (1) has been disclosed by F. Macchia and L. Turbanti in the Italian patent application Ser. No. 50,115 A/74, filed Apr. 4, 1974.

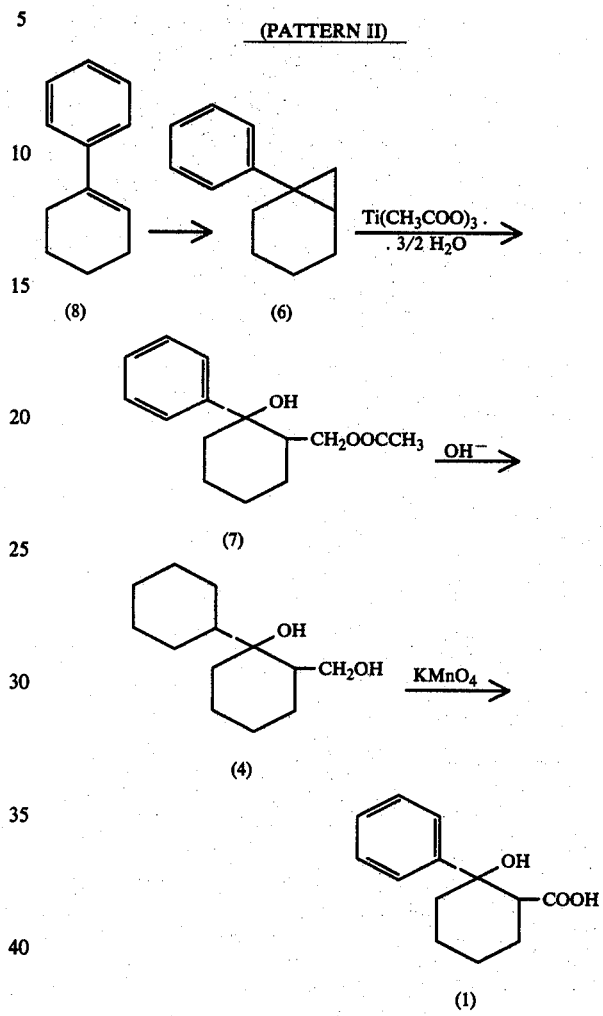

According to the above process, the acid (1) is prepared through the following reaction sequence: by oxidizing 1-phenyl [4.1.0]-bicycloheptane (6) with thallium acetate (trivalent thallium) in an aprotic solvent having a low polarity, the monoacetyl derivatives (7) is obtained, which, by alkaline hydrolysis, gives the diol (4): the latter, by being oxidized with potassium permanganate, is then converted to the acid having the formula (1):

The method for preparing the acid (1) as disclosed by Zimmerman and English (See Pattern I) is affected by a few drawbacks. The first intermediate (3), i.e. 2-hydroxymethyl-cyclohexanone, is thermolabile and can be obtained in a pure state with difficulty with satisfactory yields, even when molecular distillation apparatus are adopted.

The conversion of the compound (3) into the diol (4) occurs with extremely low yields (26% approx. of theory related to the compound (3) even if a very strong excess is used (up to 300% and over) of the Grignard reactant (PhMgBr).

In addition, the latter reaction is not completely stereo-selective and is converted, along with other by-products, to the diol of formula (5):

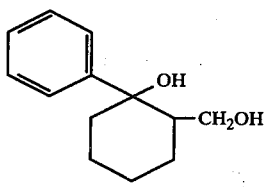

which is a diastereoisomer of that of formula (4). This fact thus makes essential to purify the intermediate (4) prior to oxidizing thereof into the final compound (1).

The synthesizing method as disclosed in the Italian Patent Application aforementioned, while enabling the diol (4) to be obtained in a thoroughly stereo-selective fashion, involves a few inconveniences in the industrial application. The starting product of the synthesis, i.e. 1-phenyl-[4.1.0]bicycloheptane (6), is prepared (Yu. S. Shabarov et al., C.A., 68, 21607 (1968)) with a 66% yield, starting from 1-phenyl-cyclohexene (8), by a reaction which requires the use of a reactant, methylene iodide, which is expensive and cannot be recovered. In addition, in order that the compound (6) may be converted into the monoacetate (7) the use is necessary of considerable amounts (up to twice the theoretical amount) of the deadly thallium salt.

The principal object of the present invention is to provide a novel method whereby the expected acid (1) may be obtained in the state of purity and in a simpler and cheaper way.

A more detailed object of the present invention is to provide a method for obtaining the fundamental intermediate for the synthesis of the acid (1), that is to say, the 1-phenyl-cis-2-hydroxymethyl-r-1-cyclohexanol (4) in a highly stereo-selective manner and via a route which is simpler and cheaper than those of the prior art.

In order that the aforementioned objects may be achieved, the method according to the present invention comprises the following steps:

the reaction of 1-phenylcyclohexene (8) with formaldehyde in formic acid, or in admixture of formic acid with other solvents;

the alkaline hydrolysis of the reaction mixture, the result being the virtually exclusive obtention of 1-phenyl-cis-2-hydroxymethyl-r-1-cyclohexanol (4) and of 4-phenyl-cis-4,5-tetramethylene-1,3-dioxan (9);

separation of the diol (4) from the dioxan (9) and subsequent oxidizing of the diol with potassium permanganate. Thus, the present invention is summarized in the reactions reported in the Pattern III hereunder:

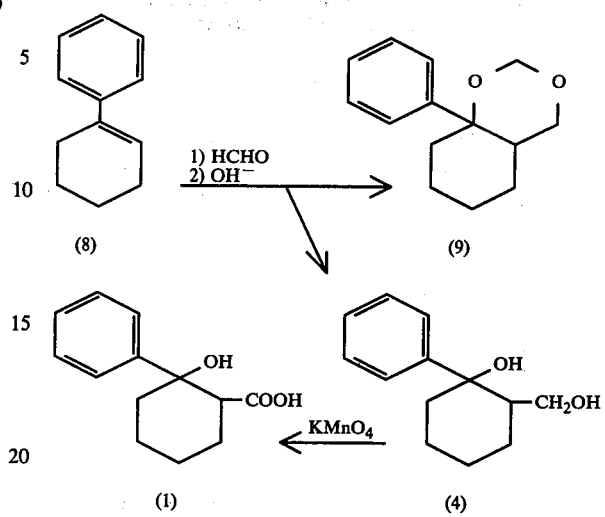

PATTERN III

The reaction of 1-phenylcyclohexane (8) with formaldehyde had already been described (G. Lippi, B. Macchia and M. Pannocchia, Gazz. Chim. Ital., 100, 14 (1970)). However, under the conditions disclosed there (acetic acid as the solvent and sulphuric acid as the catalyst), which are those as generally used for this kind of reaction (Prins' reaction), intricate mixtures of compounds were obtained, in which the dioxan (9) was found, but no diol (4) was absolutely present, the same being true of the compounds from which said dioxan (9) could have been obtained.

According to the present invention, the following results have been obtained for the first time, namely:

(A) The reaction has been carried out of 1-phenylcyclohexene (8) with formaldehyde in formic acid or admixtures thereof with other solvents (of the kind of water, acetic acid, chloroform, benzene, dioxan, tetrahydrofuran, ethyl ether);

(B) there has been obtained, from the reaction of 1-phenylcyclohexene (8) with formaldehyde, the 1-phenyl-cis-2-hydroxylmethyl-r-1-cyclohexanol (4);

(C) it has been possible, by varying the concentration and the type of formaldehyde, to obtain virtually exclusive mixtures of the diol (4) and the dioxan (9) having different compositions.

The unusual merits of the present invention is primarily in that the diol (4) can be obtained with good yields and directly from 1-phenylcyclohexene (8) (a product which is a cheap starter) by adopting an extremely simple procedure, the latter requiring but the use of cheap reactants and solvents which, moreover, can be recovered, such a procedure, in addition, being susceptible of being reduced to practice with extremely cheap implementations and apparatus, the times required for its performance being very short.

The invention will now be described in more detail by the ensuing examples, which are nonlimiting: of them, Examples 1 and 2 are illustrative of procedures which are conducive with good yields, to the diol (4) then to its conversion into the acid (1), whereas Example 3 is an illustration of the reaction conditions under which a high percentage of the dioxan (9) can be obtained.

An essential prerequisite is that 1-phenylcyclohexene (8) is prepared after the method of E. W. Garbish, Jr., J. Org. Chem., 26, 4165 (1961).

EXAMPLE 1

(A) Reaction of 1-phenylcyclohexene (8) with formaldehyde, in an admixture of formic acid and water To a stirred slurry of 95 grams (0.60 mol) of 1-phenylcyclohexene (8) in a solution of 600 mls of 99% formic acid and of 20 mls water, are added 63 mls of an aqueous 40% formaldehyde solution (weight/volume) (0.84 mol) and stirring is continued at room temperature during 3 hours. The reaction mixture is then evaporated under reduced pressures and at room temperature, the residue thus obtained being treated with a solution of 40 grams of NaOH (scales) in 300 mls ethanol and 100 mls water. The mixture is diluted with water and extracted with chloroform. The chloroform extracts are washed with water and evaporated to dryness. The residue, taken up with petroleum ether (b.p. 40° C.–70° C.) (500 mls approx.), crystallizes to give 58 grams (0.28 mol) of virtually pure diol (4), m.p. 82° C.–83° C. (Yield 47% of theory, approx.).

Upon evaporation of the mother liquors of the diol (4), a residue is obtained, which is nearly exclusively constituted by the dioxan (9), wherefrom, by crystallization from ethanol, are obtained 52 grams of the pure dioxan (9), m.p. 61° C.–62° C.

(B) Oxidation of the diol (4) to the cis-2-hydroxy-2-phenyl-r-1-cyclohexanecarboxylic acid (1)

To a slurry of 58 grams (0.28 mol) of diol (4) in 3,000 mls of water at 85° C., is added, during 20 mins., with stirring, an intimate mixture of 58 grams of $Na_2CO_3$ and 115 grams of $KMnO_4$. Stirring is continued during 30 mins. whereafter manganese dioxide is collected on a filter and washed with about 300 mls hot water. Both the filtrate and the washing liquors are acidified, combined and cooled to room temperature, using diluted HCl down to a pH of 1.5–2: the acid (1) precipitates and is collected on a filter, washed with water and dried at 60° C. in a vacuo. There are thus obtained 49.5 grams (about 0.22 mol) of pure acid (1), having a m.p. of 146° C.–147° C. (yield 80% of theory).

EXAMPLE 2

(A) Reaction of 1-phenylcyclohexene (8) with formaldehyde in an admixture of formic acid-acetic acid-water.

To a stirred slurry of 95 grams (0.60 mol) of 1-phenylcyclohexene (8) in a solution of 300 mls of 99% formic acid and 300 mls of glacial acetic acid are added 63 mls of a 40% aqueous solution of formaldehyde (weight/volume) (0.84 mol) and stirring is continued at room temperature for 6 hours.

The reaction mixture is then evaporated under reduced pressures and the so-obtained residue is treated as disclosed in Example 1, under A). Upon crystallization, there are obtained 60 grams (0.29 mol) of the diol (4) (yield about 48% of theory) and 49 grams (0.22 mol) of the dioxan (9) (yield about 37% of theory). The diol (4) is then converted into the acid (1° as described in Example 1 at B).

EXAMPLE 3

Reaction of the 1-phenylcyclohexene (8) with formaldehyde in formic acid

To a stirred slurry of 95 grams (0.60 mol) of 1-phenylcyclohexene (8) in 600 mls of 99% formic acid are added 54 grams (1.80 mol) of paraformaldehyde and stirring is continued at room temperature during 24 hours. The reaction mixture is then evaporated under reduced pressures and the residue thus obtained, which is essentially constituted by the dioxan (9) is crystallized from ethanol to give 118 grams (0.54 mol) of dioxan (9) which is virtually pure, m.p. 61° C.–62° C. (yield about 90% of theory). The method according to the present invention has been described to a preferred embodiment, it being understood that substantially equivalent changes lie within the scope of this invention.

What we claim is:

1. A method for the preparation of cis-2-hydroxy-2-phenyl-r-1-cyclohexanecarboxylic acid comprising the steps of (1) reacting 1-phenyl cyclohexene with formaldehyde in the presence of formic acid; (2) hydrolyzing the reaction product of (1) is an alkaline medium to provide a mixture of 1-phenyl-cis-2-hydroxymethyl-r-1-cyclohexanol and 4-phenyl-cis-4,5-tetramethylene-1,3-dioxan; (3) separating said cyclohexanol from said dioxan; and (4) oxidizing said cyclohexanol to said carboxylic acid.

2. The method of claim 1 wherein said formic acid is in admixture with a solvent.

3. The method of claim 2 wherein said solvent is a member of the group consisting of water, acetic acid, chloroform, benzene, dioxan, tetrahydrofuran, and ethyl ether.

4. The method of claim 2 wherein said solvent is a mixture of water and acetic acid.

5. The method of claim 1 wherein the oxidizing agent is potassium permanganate.

6. The method of producing 1-phenyl-cis-2-hydroxymethyl-r-1-cyclohexanol comprising the steps of (1) reacting 1-phenyl cyclohexene with formaldehyde in the presence of formic acid; (2) hydrolyzing the reaction product of (1) in an alkaline medium to provide a mixture of 1-phenyl-cis-2-hydroxymethyl-r-1-cyclohexanol and 4-phenyl-cis-4,5-tetramethylene-1,3-dioxan, and (3) separating said cyclohexanol from said dioxan.

7. The process of claim 6 wherein said formic acid is in admixture with a member of the group consisting of water, acetic acid, chloroform, benzene, dioxan, tetrahydrofuran, and ethyl ether.

8. The method of preparing 4-phenyl-cis-4,5-tetramethylene -1,3-dioxan in the substantially pure state comprising reacting 1-phenyl cyclohexene with a large excess of formaldehyde in the presence of formic acid and recovering said 4-phenyl-cis-4,5-tetramethylene-1,3-dioxan from said reaction mixture.

* * * * *